United States Patent
Lin et al.

(10) Patent No.: US 9,999,396 B2
(45) Date of Patent: *Jun. 19, 2018

(54) EXERCISE PHYSIOLOGICAL SENSING SYSTEM, MOTION ARTIFACT SUPPRESSION PROCESSING METHOD AND DEVICE

(71) Applicant: Industrial Technology Research Institute, Hsinchu (TW)

(72) Inventors: Hsing-Chen Lin, Taichung (TW); Shuenn-Yuh Lee, Tainan (TW); Tzung-Min Tsai, Changhua County (TW)

(73) Assignee: Industrial Technology Research Institute, Hsinchu (TW)

( * ) Notice: Subject to any disclaimer, the term of this patent is extended or adjusted under 35 U.S.C. 154(b) by 159 days.

This patent is subject to a terminal disclaimer.

(21) Appl. No.: 14/920,901

(22) Filed: Oct. 23, 2015

(65) Prior Publication Data
US 2016/0073966 A1      Mar. 17, 2016

Related U.S. Application Data

(63) Continuation-in-part of application No. 14/519,147, filed on Oct. 21, 2014, now Pat. No. 9,895,110.

(30) Foreign Application Priority Data

Sep. 11, 2014   (TW) .............................. 103131327 A
Sep. 2, 2015    (TW) .............................. 104128988 A

(51) Int. Cl.
*A61B 5/00*   (2006.01)
*A61B 7/04*   (2006.01)
(Continued)

(52) U.S. Cl.
CPC .......... *A61B 5/7207* (2013.01); *A61B 5/7221* (2013.01); *A61B 7/04* (2013.01);
(Continued)

(58) Field of Classification Search
None
See application file for complete search history.

(56) References Cited

U.S. PATENT DOCUMENTS

| 6,783,501 B2 | 8/2004 | Takahashi et al. |
| 7,769,435 B2 | 8/2010 | Kuo et al. |

(Continued)

FOREIGN PATENT DOCUMENTS

| TW | M245952 | 10/2004 |
| TW | I222861 | 11/2004 |

(Continued)

OTHER PUBLICATIONS

"Notice of Allowance of Taiwan Counterpart Application", dated Jun. 20, 2016, p. 1-p. 3.

(Continued)

*Primary Examiner* — Erica Lee
(74) *Attorney, Agent, or Firm* — JCIPRNET

(57) ABSTRACT

An exercise physiological sensing system, a motion artifact suppression processing method and a motion artifact suppression processing device for obtaining a stable exercise heart rate signal of a user during exercise are provided. The exercise physiological sensing system includes a bone conduction body, a signal-to-noise ratio analysis module, and a computation module. The bone conduction body has a physiological sensor. The physiological sensor detects a physiological signal from a detected area of the user. The signal-to-noise ratio analysis module is coupled to the physiological sensor and detects a quality stability of the physiological signal. The computation module is coupled to (Continued)

the signal-to-noise ratio analysis module and generates the stable exercise heart rate signal according to the physiological signal. Accordingly, the exercise physiological sensing system can effectively improve the stability of the detected physiological signal during exercise.

7 Claims, 7 Drawing Sheets

(51) Int. Cl.
 *H04R 1/46* (2006.01)
 *A61B 5/024* (2006.01)
(52) U.S. Cl.
 CPC ............ *H04R 1/46* (2013.01); *A61B 5/02438* (2013.01); *A61B 5/02444* (2013.01); *A61B 5/6803* (2013.01); *A61B 5/6816* (2013.01); *A61B 5/725* (2013.01); *A61B 2562/0204* (2013.01); *A61B 2562/028* (2013.01); *H04R 2201/003* (2013.01)

(56) References Cited

U.S. PATENT DOCUMENTS

| | | | |
|---|---|---|---|
| 2003/0018274 | A1 | 1/2003 | Takahashi et al. |
| 2003/0220584 | A1* | 11/2003 | Honeyager ........ A61B 5/02125 600/559 |
| 2007/0219059 | A1 | 9/2007 | Schwartz et al. |
| 2007/0219457 | A1* | 9/2007 | Lo ........................ A61B 5/0002 600/519 |
| 2009/0060231 | A1 | 3/2009 | Buroojy |
| 2010/0016741 | A1 | 1/2010 | Mix et al. |
| 2010/0210420 | A1 | 8/2010 | Chang et al. |
| 2013/0022220 | A1 | 1/2013 | Dong et al. |

FOREIGN PATENT DOCUMENTS

| | | |
|---|---|---|
| TW | 200719867 | 6/2007 |
| TW | I316401 | 11/2009 |
| TW | 201036591 | 10/2010 |
| TW | I374726 | 10/2012 |

OTHER PUBLICATIONS

Jun Tokuda, et al., "Development of an earphone-like pulsimeter and walking application," SICE Annual Conference 2008, Aug. 20-22, 2008, pp. 2304-2307.

Masaki Shuzo, et al., "Discrimination of Eating Habits with a Wearable Bone Conduction Sound Recorder System," Sensors, 2009 IEEE, Oct. 25-28, 2009, pp. 1666-1669.

Keya Pandia, et al., "Motion Artifact Cancellation to Obtain Heart Sounds From a Single Chest-Worn Accelerometer," Acoustics Speech and Signal Processing (ICASSP), 2010 IEEE International Conference on, Mar. 14-19, 2010, pp. 590-593.

Ming-Zher Poh, et al., "Cardiovascular Monitoring Using Earphones and a Mobile Device," Pervasive Computing, IEEE, vol. 11, Issue 4, Dec. 3, 2010, pp. 18-26.

Ji Yun Shin, et al., "Development of Smartphone-based Stethoscope System," Control, Automation and Systems (ICCAS), 2013 13th International Conference on, Oct. 20-23, 2013, pp. 1288-1291.

* cited by examiner

EXERCISE PHYSIOLOGICAL SENSING SYSTEM, MOTION ARTIFACT SUPPRESSION PROCESSING METHOD AND DEVICE

CROSS-REFERENCE TO RELATED APPLICATION

This application is a continuation-in-part application of and claims the priority benefit of a prior application Ser. No. 14/519,147, filed on Oct. 21, 2014, now pending. The prior application Ser. No. 14/519,147 claims the priority benefit of Taiwan application serial no. 103131327, filed on Sep. 11, 2014. This continuation-in-part application also claims the priority benefits of Taiwan application serial no. 104128988, filed on Sep. 2, 2015. The entirety of each of the above-mentioned patent applications is hereby incorporated by reference herein and made a part of this specification.

TECHNICAL FIELD

The disclosure relates to an exercise physiological sensing system, and more particularly, relates to an exercise physiological sensing system, a motion artifact suppression processing method and a motion artifact suppression device for obtaining a stable exercise heart rate signal of a user during exercise.

BACKGROUND

In recent years, as material life improves, people have become more conscious concerning the issues of health, and thus population for engaging exercises (such as hiking, jogging, walking and biking) is also gradually increased each year. For instance, when high-intensity self-training is to be conducted, a jogger may want to know about current changes in physiological conditions and whether exercise intensity can achieve a personal fitness goal. As such, the jogger may wear various physiological recorders (e.g., a health watch, a pace recorder and a heart rate belt, etc.) in order to constantly monitor the physiological conditions. To prevent errors from occurring on exercise physiological data measured in a high-intensity exercise-training, the ancillary devices worn by the jogger must be in close contact with the skin of the jogger. However, this results in discomfort for the user during exercise and thereby reduces willingness in equipping or wearing said devices.

Accordingly, it is one of the major subjects in the industry as how solve the discomfort for the user during exercise while improving a stability of the exercise physiological data measured in the high-intensity self-training.

SUMMARY

An exercise physiological sensing system for obtaining a stable exercise heart rate signal of a user during exercise is provided according to an exemplary embodiment of the disclosure. The exercise physiological sensing system includes a bone conduction body, a signal-to-noise ratio analysis module, and a computation module. The bone conduction body has a physiological sensor. The physiological sensor detects a physiological signal from a detected area of the user. The signal-to-noise ratio analysis module is coupled to the physiological sensor and detects a quality stability of the physiological signal. The computation module is coupled to the signal-to-noise ratio analysis module and generates the stable exercise heart rate signal according to the physiological signal.

A motion artifact suppression processing method for processing a physiological signal detected from a detected area of a user during exercise is provided according to an exemplary embodiment of the disclosure. The motion artifact suppression processing method includes: placing an exercise digital signal corresponding to the detected area into a sample matrix and initializing a basis matrix and a coefficient matrix and normalizing the basis matrix. The motion artifact suppression processing method further includes: updating values of a plurality of elements of the basis matrix according to original values of the elements of the basis matrix and updating values of a plurality of elements of the coefficient matrix according to original values of the elements of the coefficient matrix. The motion artifact suppression processing method further includes: when the values of the elements in both the basis matrix and the coefficient matrix are fully updated, calculating a mean square error (MSE) according to the basis matrix, the coefficient matrix and the sample matrix, and obtaining a motion artifact and an exercise heart rate signal according to the mean square error. If the values of the elements in both the basis matrix and the coefficient matrix are not yet fully updated, the operation of updating the values of the elements of the basis matrix according to the original values of the elements of the basis matrix and updating the values of the elements of the coefficient matrix according to the original values of the elements of the coefficient matrix is re-executed.

A motion artifact suppression processing device for processing a physiological signal detected from a detected area of a user during exercise is provided according to an exemplary embodiment of the disclosure. The motion artifact suppression processing device includes a signal input module, a processing and computation module, and a signal output module. The signal input module receives an exercise digital signal corresponding to the detected area. The processing and computation module is coupled to the signal input module and places the exercise digital signal corresponding to the detected area into a sample matrix. In addition, the processing and computation module further initializes a basis matrix and a coefficient matrix and normalizes the basis matrix. Furthermore, the processing and computation module further updates values of a plurality of elements of the basis matrix according to original values of the elements of the basis matrix and updates values of a plurality of elements of the coefficient matrix according to original values of the elements of the coefficient matrix. When the values of the elements in both the basis matrix and the coefficient matrix are fully updated, the processing and computation module further calculates a mean square error according to the basis matrix, the coefficient matrix and the sample matrix, and obtains a motion artifact and an exercise heart rate signal according to the mean square error. The signal output module is coupled to the processing and computation module and output the motion artifact and the exercise heart rate signal. If the values of the elements in both the basis matrix and the coefficient matrix are not yet fully updated, the operation of updating the values of the elements of the basis matrix according to the original values of the elements of the basis matrix and updating the values of the elements of the coefficient matrix according to the original values of the elements of the coefficient matrix is re-executed by the processing and computation module.

To make the above features and advantages of the disclosure more comprehensible, several embodiments accompanied with drawings are described in detail as follows.

BRIEF DESCRIPTION OF THE DRAWINGS

The accompanying drawings are included to provide a further understanding of the disclosure, and are incorporated in and constitute a part of this specification. The drawings illustrate embodiments of the disclosure and, together with the description, serve to explain the principles of the disclosure.

DETAILED DESCRIPTION

Figure 1:
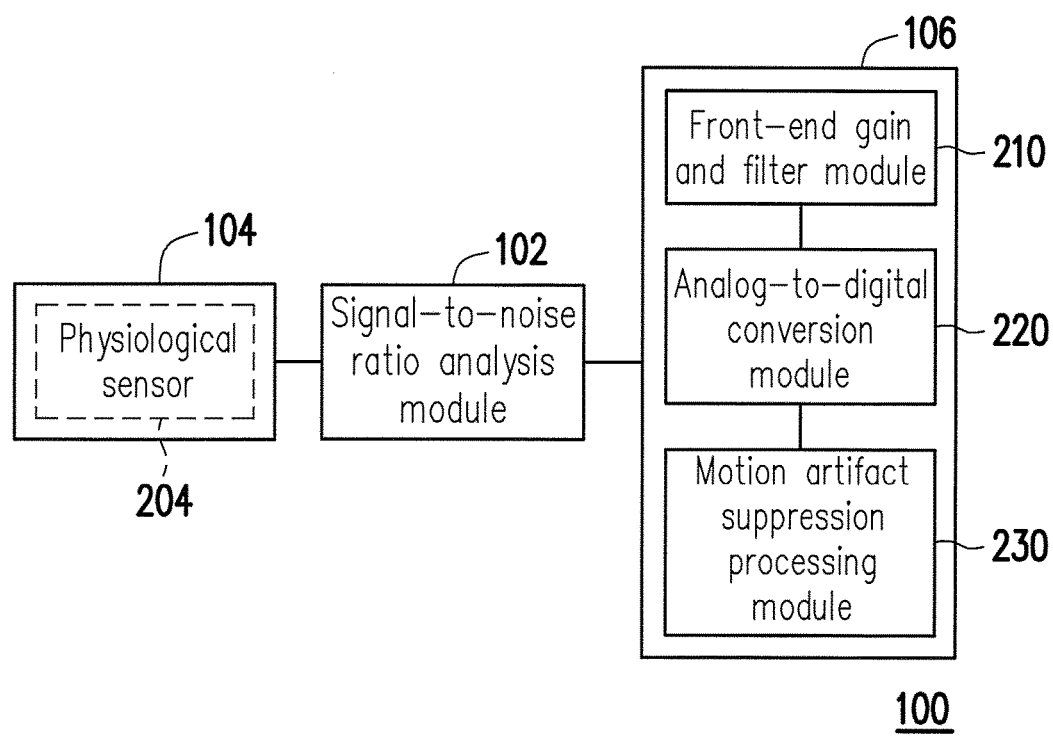
FIG. 1 is a schematic diagram illustrating an exercise physiological sensing system according to a first exemplary embodiment.

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

The disclosure is an exercise physiological sensing system, a motion artifact suppression processing method and a motion artifact suppression processing device, which are capable of stably monitoring exercise physiological conditions of users during exercise.

The exercise physiological sensing system, the motion artifact suppression processing method and the motion artifact suppression processing device proposed according to the exemplary embodiments of the disclosure are capable of improving the stability of the exercise physiological data detected in the high-intensity exercise training.

First Exemplary Embodiment

FIG. 1 is a schematic diagram illustrating an exercise physiological sensing system according to a first exemplary embodiment.

Referring to FIG. 1, an exercise physiological sensing system 100 may be used to obtain a stable exercise heart rate signal of a user during exercise, and assist the user to detect and process a physiological signal during exercise. For example, the exercise physiological sensing system 100 may be implemented in an exercise physiological sensing device used in various exercises such as a stepping exercise, a running exercise a jogging exercise or a biking exercise, but the disclosure is not limited to thereto. In the exemplary embodiment, the exercise physiological sensing system 100 includes a bone conduction body 104, a signal-to-noise ratio analysis module 102, and a computation module 106.

The bone conduction body 104 has a physiological sensor 204. For example, in the exemplary embodiment, the physiological sensor 204 is a bone conduction microphone or sensor, and the physiological sensor 204 detects a corresponding physiological signal from a temporal bone portion of the user. The bone conduction microphone receives a sound signal of bone vibration through skin conduction with the temporal bone portion of the user. Therefore, interferences of sounds from both the human body and the outside can be effectively reduced. In other words, by utilizing a characteristic of excellent anti-noise interference provided by the bone conduction microphone, a process of noise elimination may be performed on the received physiological signal of the temporal bone portion in advance.

The signal-to-noise ratio analysis module 102 is coupled to the physiological sensor 204 and configured to detect a quality stability of the physiological signal received by the physiological sensor 204. For example, in the exemplary embodiment, the physiological signal corresponding to the temporal bone portion is detected by the bone conduction microphone. Therefore, the physiological sensor 204 can determine that the quality stability of the physiological signal is good.

The computation module 106 is coupled to the signal-to-noise ratio analysis module 102 and configured to generate the stable exercise heart rate signal according to the physiological signal received by the signal-to-noise ratio analysis module 102.

For example, in the exemplary embodiment, the computation module 106 includes a front-end gain and filter module 210, an analog-to-digital conversion module 220 and a motion artifact suppression processing module 230.

The front-end gain and filter module 210 filters and amplifies the physiological signal received by the signal-to-noise ratio analysis module 102 in order to generate an exercise analog signal corresponding to the temporal bone portion, and transmits the exercise analog signal corresponding to the temporal bone portion to the analog-to-digital conversion module 220. The analog-to-digital conversion module 220 converts the exercise analog signal corresponding to the temporal bone portion into an exercise digital signal corresponding to the temporal bone portion, and transmits the exercise digital signal corresponding to the temporal bone portion to the motion artifact suppression processing module 230. Thereafter, the motion artifact suppression processing module 230 further decomposes the exercise digital signal corresponding to the temporal bone portion at least into a motion artifact and an exercise heart rate signal, and eliminates the decomposed motion artifact from the exercise digital signal corresponding to the temporal bone portion in order to obtain the stable exercise heart rate signal.

The motion artifact suppression processing module 230 in the computation module 106 of the disclosure is implemented by software modules or program codes. For example, the exercise physiological sensing system 100 includes a processor circuit (not illustrated) and a storage circuit (not illustrated) that is configured to store the program codes for executing functions of the motion artifact suppression processing module 230 in the computation module 106. Later, when the exercise physiological sensing system 100 is enabled, the software program codes are loaded from the storage circuit and executed by the processor circuit in order to perform the functions of the motion artifact suppression processing module 230 in the computation module 106. However, the disclosure is not limited thereto. For example, in another exemplary embodiment of the disclosure, the signal-to-noise ratio analysis module 102, the computation module 106 as well as the front-end gain and filter module 210, the analog-to-digital conversion module 220 and the motion artifact suppression processing module 230 thereof may be implemented by hardware circuits. For example, functions of the signal-to-noise ratio analysis module 102, the computation module 106, the front-end gain and filter module 210, the analog-to-digital conversion module 220 and the motion artifact suppression processing module 230 may be implemented by the hardware circuits to become a signal-to-noise ratio analysis circuit, a computation circuit, a front-end gain filter circuit, an analog-to-digital conversion circuit and a motion artifact suppression processing circuit.

For clear description, in the exemplary embodiment, an exercise physiological sensing device implemented for the user to conduct a running exercise is provided below as an example for detailed description.

Figure 2A:
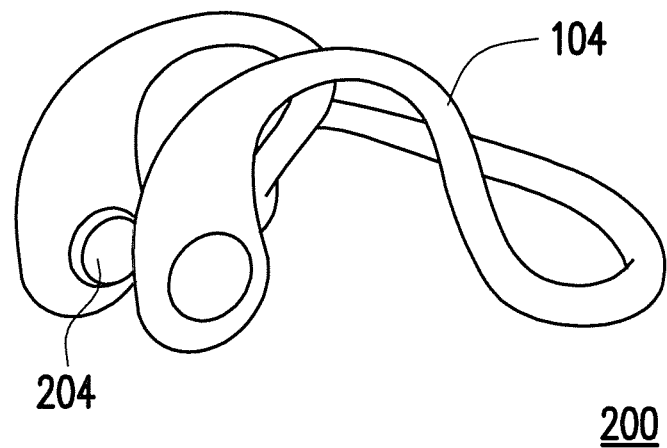
FIG. 2A, FIG. 2B and FIG. 2C are schematic diagrams illustrating the exercise physiological sensing system implemented in an exercise physiological sensing device according to the first exemplary embodiment.
Figure 2B:
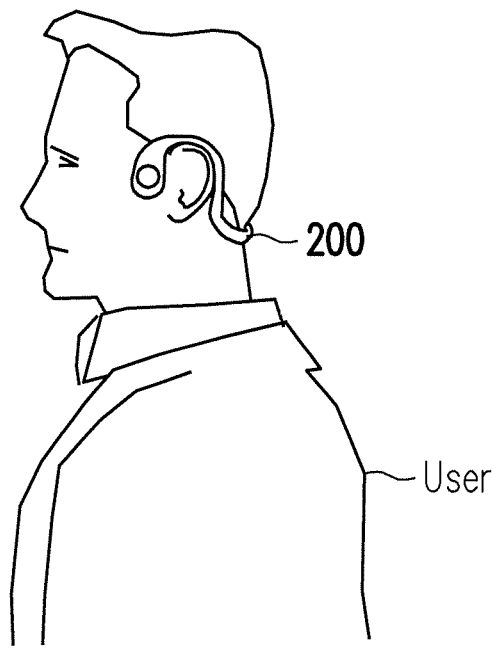
Figure 2C:
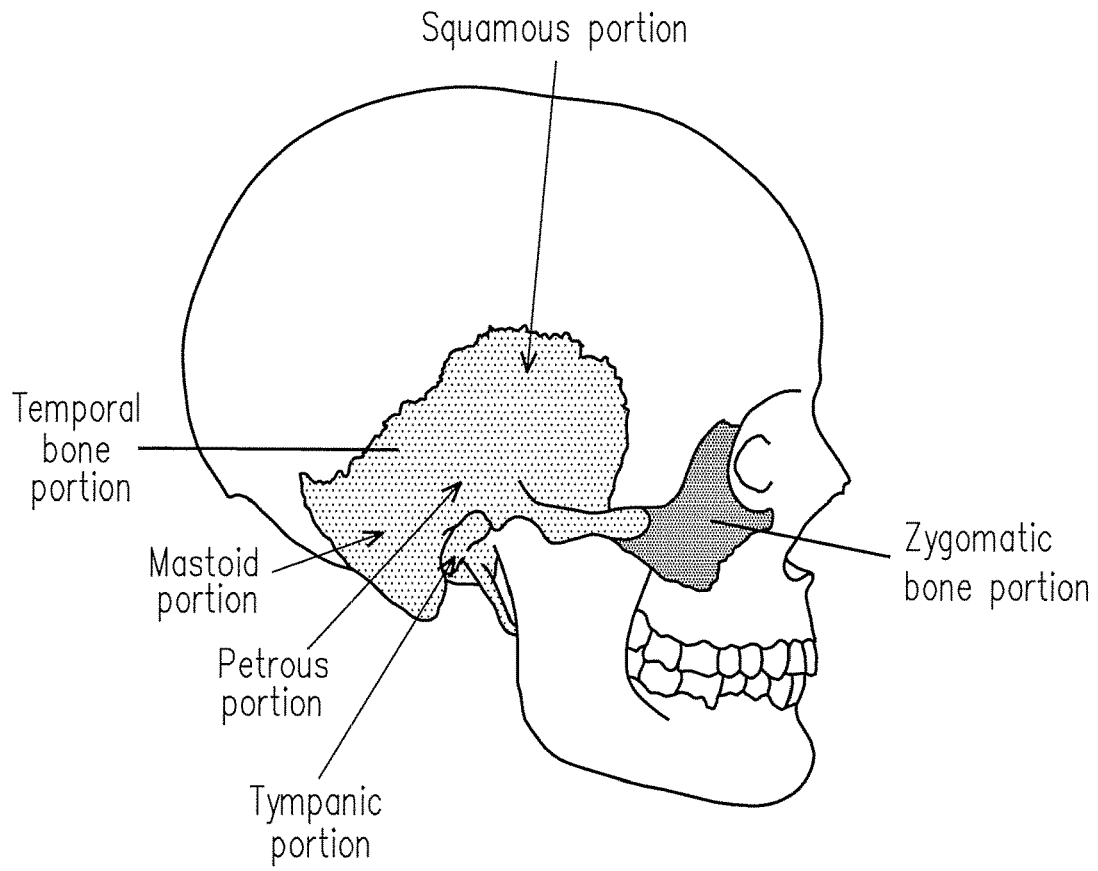

FIG. 2A is a schematic diagram illustrating the exercise physiological sensing system implemented in an exercise physiological sensing device according to the first exemplary embodiment, and FIG. 2B and FIG. 2C illustrate schematic diagrams for equipping the exercise physiological sensing device.

Referring to FIG. 2A, FIG. 2B and FIG. 2C, an exercise physiological sensing device 200 is configured to be worn by the user during exercise.

In the exemplary embodiment, the bone conduction body 104 of the exercise physiological sensing system 200 is a mobile device, and can functions of playing music or radio programs. After the exercise physiological sensing device 200 is worn on the head of the user, the physiological sensor 204 of the bone conduction body 104 is attached closely to a detected area between the eye and the ear of the user, so as to continuously monitor physiological conditions of the user during exercise while providing the user the functions of playing music or radio programs. In an exemplary embodiment, the detected area is located at the temporal bone portion. For example, the exercise physiological sensing system 100 may be attached closely to a squamous portion, a mastoid portion, a tympanic portion or a petrous portion of the temporal bone portion. For illustrative convenience, description is given below by using the temporal bone portion of the user to serve as the detected area. Nevertheless, it should be understood that the disclosure is not limited thereto. In another exemplary embodiment, the detected area may also be located at a zygomatic bone portion.

The mobile device can be connected to an electronic device (e.g., a personal digital assistant (PDA), a notebook computer, a tablet computer or a desktop computer, etc.) in wired or wireless manners. Accordingly, the user is able to instantly obtain and store the stable exercise heart rate signal during exercise. Particularly, with the disposition of the mobile device, the user can also be aware of surrounding sounds, so that the safety during exercise can be improved.

Figure 3:
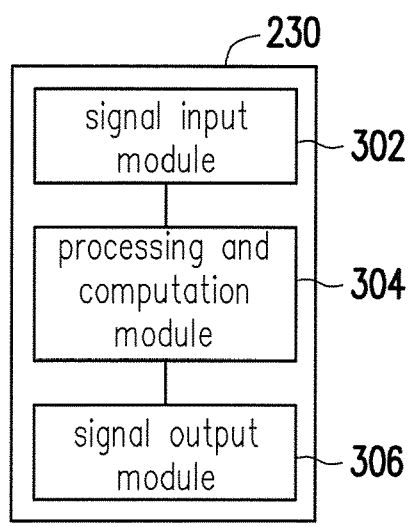
FIG. 3 is a block diagram illustrating the motion artifact suppression processing module according to the first exemplary embodiment.

FIG. 3 is a block diagram illustrating the motion artifact suppression processing module according to the first exemplary embodiment.

Referring to FIG. 3, the motion artifact suppression processing module 230 includes a signal input module 302, a processing and computation module 304, and a signal output module 306. The signal input module 302 receives the exercise digital signal corresponding to the temporal bone portion from the analog-to-digital conversion module 220, and transmits the exercise digital signal corresponding to the temporal bone portion to the processing and computation module 304. The processing and computation module 304 is coupled to the signal input module 302, and the signal output module 306 is coupled to the processing and computation module 304.

In the exemplary embodiments of the disclosure, the operation of the motion artifact suppression processing module 230 for decomposing the exercise digital signal corresponding to the temporal bone portion at least into the motion artifact and the exercise heart rate signal includes the following. First of all, the processing and computation module 304 places the exercise digital signal corresponding to the temporal bone portion into a sample matrix. Subsequently, the processing and computation module 304 initializes a basis matrix and a coefficient matrix and normalizes the basis matrix. Thereafter, the processing and computation module 304 updates values of a plurality of elements of the basis matrix according to original values of the elements of the basis matrix and updates values of a plurality of elements of the coefficient matrix according to original values of the elements of the coefficient matrix. When the values of the elements in both the basis matrix and the coefficient matrix are fully updated, the processing and computation module 304 further calculates a mean square error according to the basis matrix, the coefficient matrix and the sample matrix. Then, the processing and computation module 304 obtains the motion artifact and the exercise heart rate signal according to the mean square error, and the motion artifact and the exercise heart rate signal are outputted by the signal output module 306.

In the operation of the processing and computation module 304 for initializing the basis matrix and the coefficient matrix, the processing and computation module 304 ensures that values of a plurality of elements in both the basis matrix and the coefficient matrix are not negative values. Moreover, in the operation of the processing and computation module 304 for normalizing the basis matrix, the processing and computation module 304 normalizes a column vector of the basis matrix until a sum of a plurality of elements corresponding to the column vector is 1.

When the values of the elements in both the basis matrix and the coefficient matrix are fully updated, the processing and computation module 304 replaces the original values of the elements in both the basis matrix and the coefficient matrix respectively by the updated values of the elements. Thereafter, the processing and computation module 304 also executes the operation of normalizing the basis matrix in order to normalize the column vector of the basis matrix until the sum of the elements corresponding to the column vector is 1. Further, the processing and computation module 304 calculates the mean square error according to a product of the basis matrix and the coefficient matrix and the sample matrix. If the values of the elements in both the basis matrix and the coefficient matrix are not yet fully updated, the processing and computation module 304 continues to execute the operation of updating the values of the elements of the basis matrix according to the original values of the elements of the basis matrix and updating the values of the elements of the coefficient matrix according to the original values of the elements of the coefficient matrix until the values of all the elements in the basis matrix and the coefficient matrix are fully updated.

In the operation of obtaining the motion artifact and the exercise heart rate signal according to the mean square error, if the mean square error is 0 or a value of the mean square error is no longer changing, the processing and computation module 304 obtains the motion artifact and the exercise heart rate signal according to the current basis matrix, the current coefficient matrix and the current sample matrix. Otherwise, if the mean square error is not 0 or the value of the mean square error is constantly changing, the processing and computation module 304 re-executes the operation of updating the values of the elements of the basis matrix according to the original values of the elements of the basis matrix and updating the values of the elements of the coefficient matrix according to the original values of the elements of the coefficient matrix.

Aforementioned operations for updating the basis matrix and the coefficient matrix may be represented by formula (1), formula (2) and formula (3) below:

$$\underline{W}_{ia}^{new} \leftarrow \underline{W}_{ia} \sum_{u=1}^{m} \frac{v_{iu}}{(WH)_{iu}} H_{au} \quad (1)$$

$$\underline{W}_{ia}^{new} \leftarrow \frac{\underline{W}_{ia}}{\sum_{j}^{n} \underline{W}_{ja}} \quad (2)$$

$$H_{au}^{new} \leftarrow H_{au} \sum_{i=1}^{n} \underline{W}_{ia} \frac{v_{iu}}{(WH)_{iu}} \quad (3)$$

Herein, $\underline{V}_{n \times m}$ is the sample matrix, $\underline{W}_{n \times r}$ is the basis matrix and $\underline{H}_{r \times m}$ is the coefficient matrix. After the basis matrix $\underline{W}_{n \times r}$ and the coefficient matrix $\underline{H}_{r \times m}$ are initialized and normalized, the processing and computation module 304 continuously updates the basis matrix $\underline{W}_{n \times r}$ and the coefficient matrix $\underline{H}_{r \times m}$ respectively by using an iterative process.

Based on requirements in the application of the motion artifact suppression processing method of the exemplary embodiment, the operation of decomposing for two signals (r=2) including the motion artifact and the exercise heart rate signal is described by using the flows provided below.

Figure 4:
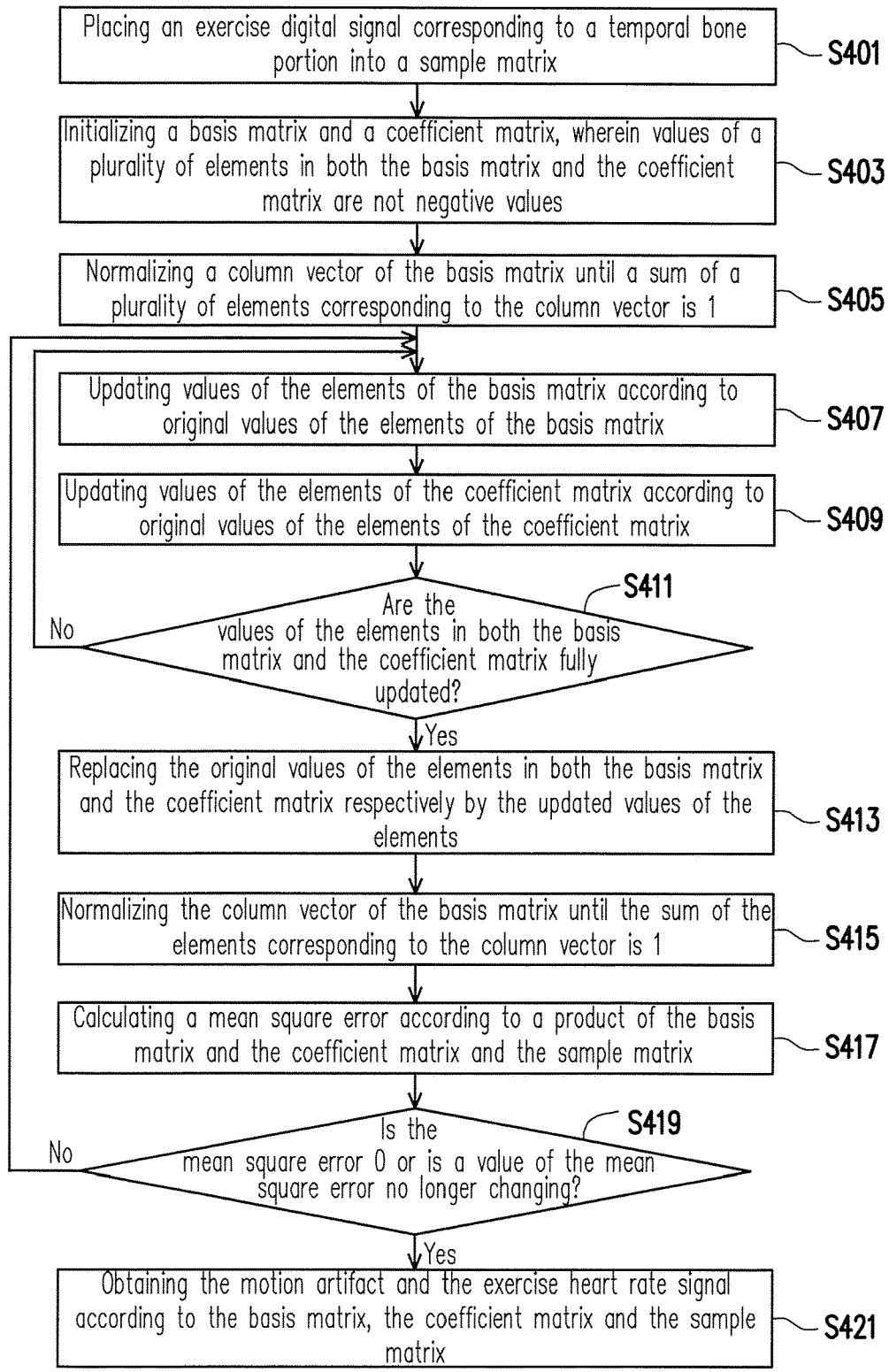
FIG. 4 is a flowchart illustrating a motion artifact suppression processing method according to the first exemplary embodiment.

FIG. 4 is a flowchart illustrating a motion artifact suppression processing method according to the first exemplary embodiment.

Referring to FIG. 4, first, in step S401, the processing and computation module 304 places an exercise digital signal corresponding to a temporal bone portion into a sample matrix.

Subsequently, in step S403, the processing and computation module 304 initializes a basis matrix and a coefficient matrix. For example, the processing and computation module 304 initializes the basis matrix and the coefficient matrix such that values of a plurality of elements in both matrices are not negative values. In other word, the values of the elements in the basis matrix and the coefficient matrix are all greater than or equal to 0.

In step S405, the processing and computation module 304 normalizes a column vector of the basis matrix until a sum of a plurality of elements corresponding to the column vector is 1.

In step S407, the processing and computation module 304 updates values of a plurality of elements of the basis matrix according to original values of the elements of the basis matrix. In step S409, the processing and computation module 304 updates values of a plurality of elements of the coefficient matrix according to original values of the elements of the coefficient matrix.

In step S411, the processing and computation module 304 determines whether the values of the elements in both the basis matrix and the computation module are fully updated.

If the values of the elements in both the basis matrix and the coefficient matrix are not yet fully updated, go back to step S407 and step S409, so that the processing and computation module 304 can re-execute the operation of updating the values of the elements of the basis matrix according to the original values of the elements of the basis matrix and updating the values of the elements of the coefficient matrix according to the original values of the elements of the coefficient matrix until the values of all the elements in the basis matrix and the coefficient matrix are fully updated.

If the values of the elements in both the basis matrix and the coefficient matrix are fully updated, in step S413, the processing and computation module 304 replaces the original values of the elements in both the basis matrix and the coefficient matrix respectively by the updated values of the elements.

In step S415, the processing and computation module 304 further normalizes the column vector of the basis matrix until the sum of the elements corresponding to the column vector is 1.

In step S417, the processing and computation module 304 further calculates a mean square error according to a product of the basis matrix and the coefficient matrix and the sample matrix.

Thereafter, in step S419, the processing and computation module 304 determines whether the mean square error is 0 or whether a value of the mean square error is no longer changing.

If the mean square error is not 0 or the value of the mean square error is constantly changing, go back to step S407 and step S409, so that the processing and computation module 304 can re-execute the operation of updating the values of the elements of the basis matrix according to the original values of the elements of the basis matrix and updating the values of the elements of the coefficient matrix according to the original values of the elements of the coefficient matrix until the values of all the elements in the basis matrix and the coefficient matrix are fully updated.

Otherwise, if the mean square error is 0 or the value of the mean square error is no longer changing, the processing and computation module 304 obtains the motion artifact and the exercise heart rate signal according to the basis matrix, the coefficient matrix and the sample matrix.

In other words, the processing and computation module 304 will constantly execute an iterative operation until the motion artifact and the exercise heart rate signal are obtained. That is to say, "the value of the mean square error is constantly changing" herein refers to that the value of the mean square error obtained in the current iterative operation is different from the value of the mean square error obtained in the previous iterative operation; whereas "the value of the mean square error is no longer changing" herein refers to that the value of the mean square error obtained in the current iterative operation is identical to the value of the mean square error obtained in the previous iterative operation.

The steps depicted in FIG. 4 may be implemented as a plurality of program codes or circuits, and the disclosure is not limited thereto. For example, in another exemplary embodiment, the motion artifact suppression processing module 230 may be implemented by the hardware circuits to become a motion artifact suppression processing device, and the signal input module 302, the processing and computation module 304 and the signal output module 306 may be implemented by the hardware circuits to become a signal input circuit, a processing and computation circuit and a signal output circuit.

In addition, the decomposition for the motion artifact and the exercise heart rate signal in aforementioned motion artifact suppression processing method is performed by adopting characteristics of signal separation in single channel, a constraint condition with non-negative values for the elements, feature additivity and local characterization of non-negative values for the elements and an operational property consistent with neural network. Accordingly, the motion artifact may be effectively eliminated by using the motion artifact suppression processing method and the motion artifact suppression processing device of the disclosure in order to capture the stable exercise heart rate signal.

Figure 5:
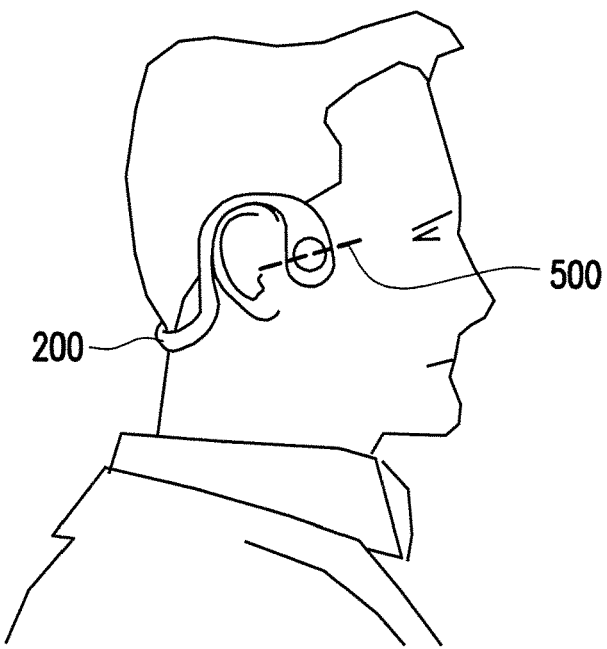
FIG. 5 is a schematic diagram illustrating detection of the physiological signal from the temporal bone portion of the user according to the first exemplary embodiment.

FIG. 5 is a schematic diagram illustrating detection of the physiological signal from the temporal bone portion of the user according to the first exemplary embodiment.

Referring to FIG. 5, an arterial system 500 of the human body operates in a region perpendicular to a carotid artery, and therefore a microvasculature will penetrate the temporal bone portion. Further, during various exercises engaged in daily lives of people, positions around the temporal bone portion or the ear are relatively more stable and have no intense actions, as compared to other body parts. That is to say, the temporal bone portion is an ideal and stable portion for exercise physiological sensing. In other words, a pulse rate can be obtained by detecting pulse beats at the temporal bone portion. For example, in the exemplary embodiments of the disclosure, in the operation of the front-end gain and filter module 210 for filtering and amplifying the physiological signal detected from the temporal bone portion in order to generate the exercise analog signal corresponding to the temporal bone portion, the front-end gain and filter module 210 captures a first heart sound signal from the received physiological signal to serve as the exercise analog signal corresponding to the temporal bone portion. For instance, heart sounds are shock waves produced when blood pass through heart. Specifically, the heart sounds are shock waves produced when valve opens and closes, or vibrations caused by myocardial contract, closing of valve, and blood impacting ventricular wall, aorta wall and the like.

Figure 6:
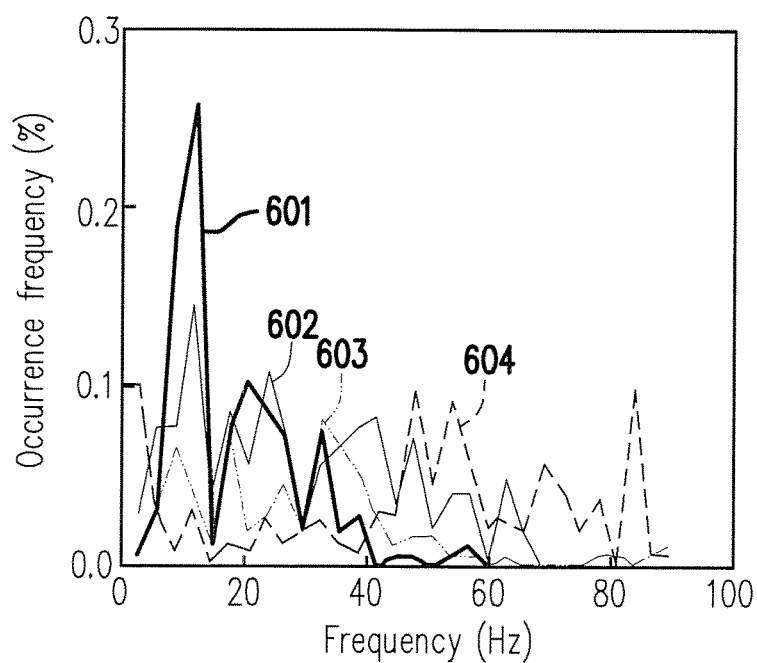
FIG. 6 is a schematic diagram illustrating a heart sound spectrum according to the first exemplary embodiment.

FIG. 6 is a schematic diagram illustrating a heart sound spectrum according to the first exemplary embodiment.

Referring to FIG. 6, two obvious heart sounds can be heard in a normal and healthy adult heart, and the two sounds sequentially occurs in each heart beat. A first of the two sounds is known as a first heat sound while a second of the two sounds is known as a second heart sound. The two heart sounds are produced by atrioventricular valve and semilunar valve, respectively. It is also possible that other sounds (e.g., murmur, a third sound being adventive sound, and a fourth heart sound with gallop rhythm) may occur in addition to said two normal sounds, The spectrum with four heart sounds as illustrated in FIG. 6 indicates frequencies for a first heart sound 601, a second heart sound 602, a third heart sound 603 and a fourth heart sound 604 to occur per one heart beat. In view of FIG. 6, it can be known that a spectral intensity of the first heart sound 601 is relatively greater, as compared to those of the second heart sound 602, the third heart sound 603 and the fourth heart sound 604. Therefore, for example, in the exemplary embodiment, the front-end gain and filter module 210 captures the first heart sound signal to serve as the exercise analog signal corresponding to the temporal bone portion. In addition, a cut-off frequency of the first heart sound 601 is approximately 16 Herz (Hz), and a signal frequency of the first heart sound 601 is below a sound frequency that the human ear can hear (20 Hz to 20000 Hz). Accordingly, the physiological signal of the user may be stably detected by combining use of the physiological sensor 204 (e.g., the bone conduction microphone).

Figure 7:
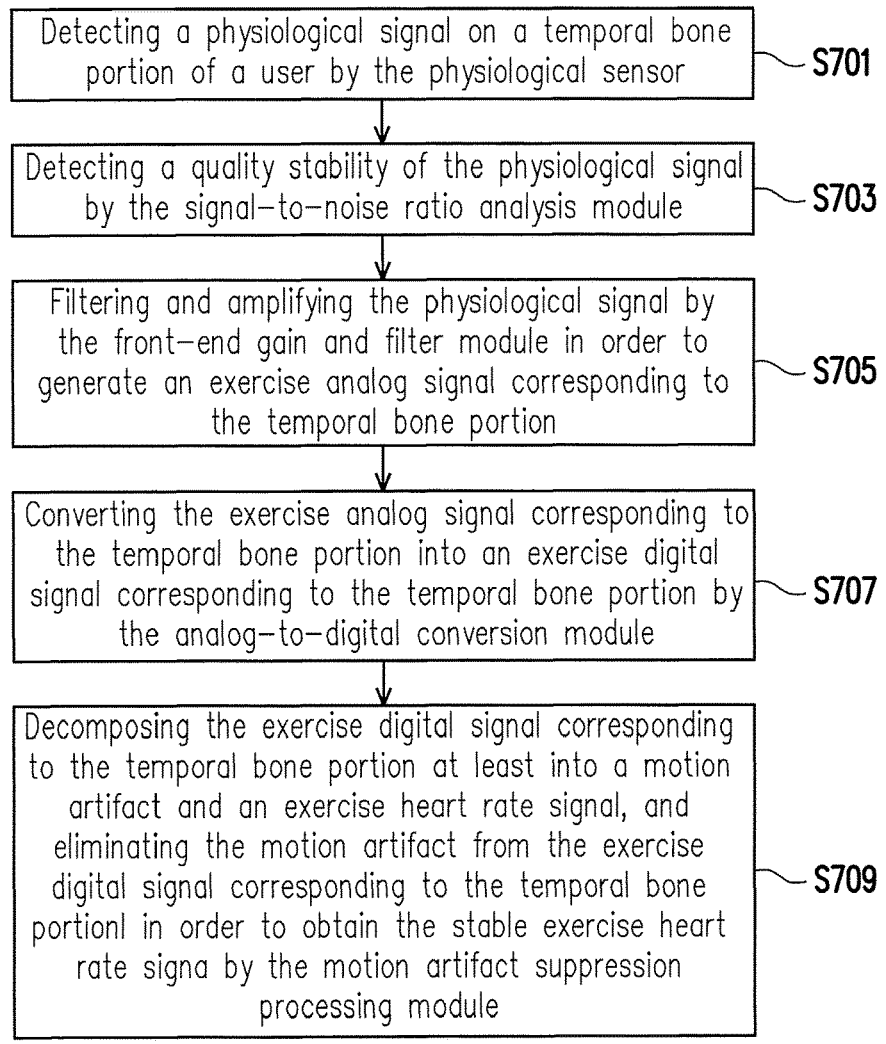
FIG. 7 is a flowchart illustrating an operation method of a physiological sensing system according to the first exemplary embodiment.

FIG. 7 is a flowchart illustrating an operation method of a physiological sensing system according to the first exemplary embodiment.

In step S701, the physiological sensor 204 (e.g., the bone conduction microphone) detects a physiological signal on a temporal bone portion of a user. In step S703, the signal-to-noise ratio analysis module 102 detects a quality stability of the physiological signal. In step S705, the front-end gain and filter module 210 filters and amplifies the physiological signal in order to generate an exercise analog signal corresponding to the temporal bone portion. In step S707, the analog-to-digital conversion module 220 converts the exercise analog signal corresponding to the temporal bone portion into an exercise digital signal corresponding to the temporal bone portion. Finally, in step S709, the motion artifact suppression processing module 230 decomposes the exercise digital signal corresponding to the temporal bone portion at least into a motion artifact and an exercise heart rate signal, and eliminates the motion artifact from the exercise digital signal corresponding to the temporal bone portion in order to obtain the stable exercise heart rate signal.

Steps depicted in FIG. 7 are described in detail as above, thus it is omitted hereinafter. It should be noted that, each of the steps depicted in FIG. 7 may be implemented as a plurality of circuits, or step S709 in FIG. 7 may be implemented as a plurality of program codes, and the disclosure is not limited thereto. Moreover, the method disclosed in FIG. 7 may be implemented with reference to above embodiments or implemented separately, and the disclosure is not limited thereto.

Second Exemplary Embodiment

A physiological sensing system of the second exemplary embodiment and an operation method thereof are essentially identical to the physiological sensing system of the first exemplary embodiment and the operation method thereof, and a difference between the two embodiments is that a physiological sensor used in the second exemplary embodiment is a micro electrical-mechanical system (MEMS) microphones. The difference between the second exemplary embodiment and the first exemplary embodiment is described below by reference with system and device structures depicted in FIG. 1, FIG. 2A to FIG. 2B, FIG. 3 and FIG. 8.

Referring back to FIG. 1, in the exemplary embodiment, the physiological sensor 204 is the MEMS microphone, and the physiological sensor 204 detects a physiological signal of a temporal bone portion of a user. The signal-to-noise ratio analysis module 102 detects a quality stability of the physiological signal received by the physiological sensor 204. Further, the computation module 106 generates a stable exercise heart rate signal according to the physiological signal received by the physiological sensor 204. In this exemplary embodiment, because the physiological sensor 204 is the MEMS microphone, the detected physiological signal has lower stability and high noise. Accordingly, the signal-to-noise ratio analysis module 102 determines that the quality of the physiological signal is poor.

Figure 8:
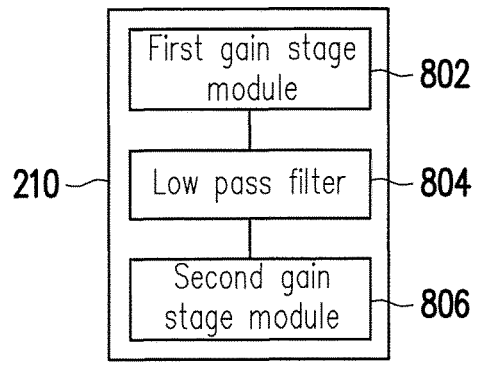
FIG. 8 is a block diagram illustrating a front-end gain and filter module according to a second exemplary embodiment.

FIG. 8 is a block diagram illustrating a front-end gain and filter module according to a second exemplary embodiment.

Referring to FIG. 8, the front-end gain and filter module 210 further includes a first gain stage module 802, a low pass filter 804 and a second gain stage module 806. Based on the above, since the physiological signal of the detected area detected by the MEMS microphone has lower stability and high noise, in the exemplary embodiment, the first gain stage module 802 in the front-end gain and filter module 210 first amplifies the physiological signal. An exercise analog signal corresponding to the temporal bone portion is captured by the low pass filter 804 from the amplified physiological signal. Herein, the exercise analog signal corresponding to the temporal bone portion captured by the low pass filter 804 is the first heart sound signal having the cutoff frequency of 16 Hz. Thereafter, the second gain stage module 806 amplifies the exercise analog signal corresponding to the temporal bone portion in order to improve the quality stability of the exercise analog signal corresponding to the temporal bone portion.

Thereafter, as identical to the first exemplary embodiment, the analog-to-digital conversion module 220 converts the processed exercise analog signal into an exercise digital signal corresponding to the temporal bone portion, and transmits the exercise digital signal corresponding to the temporal bone portion to the motion artifact suppression processing module 230. The motion artifact suppression processing module 230 decomposes the exercise digital signal corresponding to the temporal bone portion at least into a motion artifact and an exercise heart rate signal, and eliminates the motion artifact from the exercise digital signal corresponding to the temporal bone portion in order to obtain the stable exercise heart rate signal. Herein, detailed steps executed by the motion artifact suppression processing module 230 for obtaining the stable exercise heart rate signal are identical to those in the motion artifact suppression process method of the first exemplary embodiment, which are not repeated hereinafter.

In the disclosure, the front-end gain and filter module 210 as well as the first gain stage module 802 and the second gain stage module 806 thereof may be implemented by the hardware circuits to become the front-end gain filter circuit, the first gain stage circuit and the second gain stage circuit.

Figure 9:
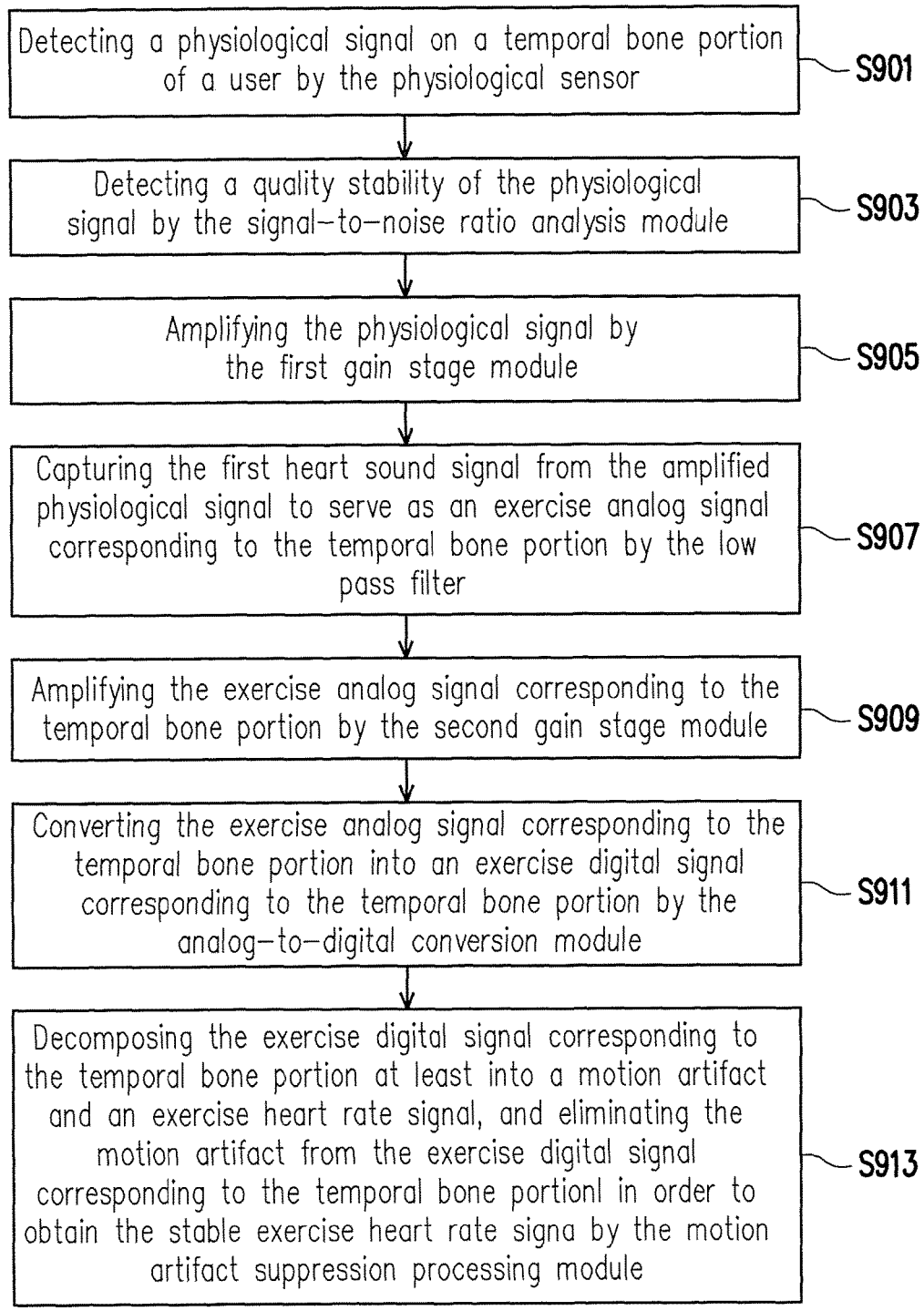
FIG. 9 is a flowchart illustrating an operation method of the physiological sensing system according to the second exemplary embodiment.

FIG. 9 is a flowchart illustrating an operation method of the physiological sensing system according to the second exemplary embodiment.

First, in step S901, the physiological sensor 204 (e.g., the MEMS microphone) detects a physiological signal on a temporal bone portion of a user. Subsequently, in step S903, the signal-to-noise ratio analysis module 102 detects a quality stability of the physiological signal. Particularly, in the exemplary embodiment, in step S905, the first gain stage module 802 in the front-end gain and filter module 210 amplifies the physiological signal. In step S907, the low pass filter 804 captures the first heart sound signal from the amplified physiological signal to serve as an exercise analog signal corresponding to the temporal bone portion. Further, in step S909, the second gain stage module 806 amplifies the exercise analog signal corresponding to the temporal bone portion. Thereafter, in step S911, the analog-to-digital conversion module 220 converts the exercise analog signal corresponding to the temporal bone portion into an exercise digital signal corresponding to the temporal bone portion. In step S913, the motion artifact suppression processing module 230 decomposes the exercise digital signal corresponding to the temporal bone portion at least into a motion artifact and an exercise heart rate signal, and eliminates the motion artifact from the exercise digital signal corresponding to the temporal bone portion in order to obtain the stable exercise heart rate signal.

Steps depicted in FIG. 9 are described in detail as above, thus it is omitted hereinafter. Each of the steps depicted in FIG. 9 may be implemented as a plurality of circuits, or step S913 in FIG. 9 may be implemented as a plurality of program codes, and the disclosure is not limited thereto. Moreover, the method disclosed in FIG. 9 may be implemented with reference to above embodiments or implemented separately, and the disclosure is not limited thereto.

In summary, the exercise physiological sensing system, the motion artifact suppression processing method and the motion artifact suppression processing device according to the disclosure are capable of providing lightweight and comfortability for the user during exercise as well as effectively improving the stability of the exercise physiological data detected in the high-intensity exercise training by detecting the physiological signal on the detected area of the user. In addition, the exercise physiological sensing system, the motion artifact suppression processing method and the motion artifact suppression processing device according to the disclosure can also provide the user the functions of playing music or radio programs while constantly monitoring the physiological conditions of the user. Since the exercise physiological sensing system and the motion artifact suppression processing device are disposed between the eye and the ear of the user (e.g., the temporal bone portion or the zygomatic bone portion), the user can also be aware of surrounding sounds accordingly, so that the safety during exercise can be improved.

It will be apparent to those skilled in the art that various modifications and variations can be made to the disclosed embodiments. It is intended that the specification and examples be considered as exemplary only, with a true scope of the disclosure being indicated by the following claims and their equivalents

The invention claimed is:

1. An exercise physiological sensing system configured to obtain a stable exercise heart rate signal of a user during exercise, and the exercise physiological sensing system comprising:
    a bone conduction body, having a physiological sensor, wherein the physiological sensor is configured to detect a physiological signal of a detected area of the user;
    a signal-to-noise ratio analysis module, coupled to the physiological sensor, wherein the signal-to-noise ratio analysis module detects a quality stability of the physiological signal; and
    a computation module, coupled to the signal-to-noise ratio analysis module, wherein the computation module generates the stable exercise heart rate signal according to the physiological signal and further comprises:
        a front-end gain and filter module for filtering and amplifying the physiological signal detected from the detected area in order to generate an exercise analog signal corresponding to the detected area;
        an analog-to-digital conversion module for converting the exercise analog signal corresponding to the detected area into an exercise digital signal corresponding to the detected area; and a motion artifact suppression processing module for decomposing the exercise digital signal corresponding to the detected area at least into a motion artifact and an exercise heart rate signal, and eliminating the motion artifact from the exercise digital signal corresponding to the detected area in order to obtain the stable exercise heart rate signal, wherein in the operation of the motion artifact suppression processing module for decomposing the exercise digital signal corresponding to the detected area at least into the motion artifact and the exercise heart rate signal, the motion artifact suppression processing module further places the exercise digital signal corresponding to the detected area into a sample matrix, wherein the motion artifact suppression processing module further initializes a basis matrix and a coefficient matrix, wherein values of a plurality of elements in both the basis matrix and the coefficient matrix are not negative values, wherein the motion artifact suppression processing module further normalizes a column vector of the basis matrix until a sum of a plurality of elements corresponding to the column vector is 1, wherein the motion artifact suppression processing module further updates the values of the elements of the basis matrix according to original values of the elements of the basis matrix and updates the values of the elements of the coefficient matrix according to original values of the elements of the coefficient matrix, wherein if the values of the elements in both the basis matrix and the coefficient matrix are fully updated, the motion artifact suppression processing module further replaces the original values of the elements in both the basis matrix and the coefficient matrix respectively by the updated values of the elements, wherein if the values of the elements in both the basis matrix and the coefficient matrix are not yet fully updated, the motion artifact suppression processing module re-executes the operation of updating the values of the elements of the basis matrix according to the original values of the elements of the basis matrix and updating the values of the elements of the coefficient matrix according to the original values of the elements of the coefficient matrix, wherein the motion artifact suppression processing module further normalizes the column vector of the basis matrix until the sum of the elements corresponding to the column vector is 1, wherein the motion artifact suppression processing module further calculates a mean square error according to a product of the basis matrix and the coefficient matrix and the sample matrix, wherein if the mean square error is 0 or a value of the mean square error is no longer changing, the motion artifact suppression processing module obtains the motion artifact and the exercise heart rate signal according to the basis matrix, the coefficient matrix and the sample matrix, wherein if the mean square error is not 0 or the value of the mean square error is constantly changing, the motion artifact suppression processing module re-executes the operation of updating the values of the elements of the basis matrix according to the original values of the elements of the basis matrix and updating the values of the elements of the coefficient matrix according to the original values of the elements of the coefficient matrix.

2. The exercise physiological sensing system as claimed in claim 1, wherein the front-end gain and filter module further captures a first heart sound signal from the detected physiological signal to serve as the exercise analog signal corresponding to the detected area.

3. The exercise physiological sensing system as claimed in claim 2, wherein a cut-off frequency of the first heart sound signal is 16 Hz.

4. The exercise physiological sensing system as claimed in claim 1, wherein the physiological sensor is a bone conduction microphone.

5. The exercise physiological sensing system as claimed in claim 1, wherein the physiological sensor is a micro electrical-mechanical system micro phone.

6. The exercise physiological sensing system as claimed in claim 1, wherein the front-end gain and filter module further comprises a first gain stage module, a second gain stage module and a low pass filter, wherein the first gain stage module amplifies the physiological signal, wherein the low pass filter captures a first heart sound signal from the amplified physiological signal to serve as the exercise analog signal corresponding to the detected area, wherein the second gain stage module amplifies the exercise analog signal corresponding to the detected area.

7. The exercise physiological sensing system as claimed in claim 1, wherein the detected area of the user is a temporal bone portion of the user or a zygomatic bone portion of the user.

* * * * *